United States Patent [19]
Demarchez et al.

[11] Patent Number: 5,827,500
[45] Date of Patent: Oct. 27, 1998

[54] PROCESS FOR IDENTIFYING RAR-RECEPTOR-ANTAGONIST COMPOUNDS

[75] Inventors: Michel Demarchez, Le Bar sur Loup; André Jomard, Saint Vallier de Thiey, both of France

[73] Assignee: Centre International de Recherches Dermatologiques Galderma, Valbonne, France

[21] Appl. No.: 665,814

[22] Filed: Jun. 19, 1996

[30] Foreign Application Priority Data

Jun. 19, 1995 [FR] France .................................. 95 07302

[51] Int. Cl.⁶ .......................... G01N 31/00; A61K 31/59; A61K 31/19
[52] U.S. Cl. .......................... 424/9.1; 514/167; 514/557; 514/568; 514/570; 436/2
[58] Field of Search .............................. 424/9.1, 9.2, 9.8, 424/9.81; 514/557, 568, 570, 167; 436/2

[56] References Cited

U.S. PATENT DOCUMENTS

| | | | |
|---|---|---|---|
| 4,889,847 | 12/1989 | Kligman | 514/171 |
| 4,992,468 | 2/1991 | Chandraratna | 514/532 |
| 5,091,518 | 2/1992 | Sucov et al. | 536/27 |
| 5,141,959 | 8/1992 | Carroll et al. | 514/568 |
| 5,612,356 | 3/1997 | Yoshimura et al. | 514/338 |
| 5,658,949 | 8/1997 | Aggarwal | 514/557 |

OTHER PUBLICATIONS

Chandraratna et al., Abstract 242 for 1996 Annual Meeting of Investigative Dermatology, *J. Invest. Derm.*, 106(4), p. 846, Apr. 1996.

Eckhardt et al., *Toxicol. Let.*, 70, pp. 299–308, Feb. 1994.

Giendimenico et al., *J. Invest. Derm.*, 102(5), pp. 676–680, May 1994.

Schiltz et al., *J. Invest. Derm.*, 87(5), pp. 663–667, Nov. 1986.

Standeven et al., *Toxicol. & Appl. Pharm.*, 138(1), pp. 169–175, May 1996.

Biochem. Biophys. Res. Commun., vol. 186, No. 2, pp. 977–983, 1992.

Biochem. Biophys. Res. Commun., vol. 179, No. 3, pp. 1554–1561, 1991.

Analytical Biochemistry, 1988, vol. 171, No. 2, pp. 238–247.

Genes Dev., 1994, vol. 8, No. 24, pp. 3068–3079.

*Primary Examiner*—Gary E. Hollinden
*Assistant Examiner*—Michael G. Hartley
*Attorney, Agent, or Firm*—Burns, Doane, Swecker & Mathis, L.L.P.

[57] ABSTRACT

The present invention relates to a process for identifying RAR-antagonist molecules, characterized in that it comprises the following steps: (i) a sufficient amount of an RAR-agonist molecule is applied topically to a part of the skin of a mammal, (ii) a molecule capable of having an RAR-antagonist activity is administered systemically or topically to this same mammal, or to this same part of the skin of the mammal, before, during or after step (i), and (iii) the response on that part of the skin of the mammal thus treated is evaluated.

8 Claims, No Drawings

PROCESS FOR IDENTIFYING RAR-RECEPTOR-ANTAGONIST COMPOUNDS

BACKGROUND OF THE INVENTION

Technical Field of the Invention

The present invention relates to a process for identifying RAR-receptor-antagonist compounds using a mammal, such as a rodent (rat, guinea pig, hamster, rabbit, mouse, etc.).

It is known that all-trans-retinoic acid is a powerful modulator (i.e. an inhibitor or, on the other hand, a stimulator, depending on the nature of the cells treated) of the differentiation and proliferation of many normal or transformed cell types. For example, it inhibits the differentiation of epithelial cells, such as epidermal keratinocytes. It also inhibits the proliferation of many transformed cells, such as melanoma cells.

Generally speaking, it is known that all-trans-retinoic acid acts on cell differentiation and proliferation by interacting with nuclear receptors known as RARs (retinoic acid receptors) contained in the cell nucleus. After binding of the ligand (i.e. the all-trans-retinoic acid), these receptors interact with the promoter region of genes controlled by retinoic acid at the level of specific response elements. In order to bind to the response elements, the RARs heterodimerize with receptors of another type known as RXRs, the natural ligand of RXRs being 9-cis-retinoic acid.

Many synthetic structural analogues of all-trans-retinoic acid or of 9-cis-retinoic acid, commonly referred to as "retinoids", have been described in the literature to date. Some of these molecules are capable of binding and activating (agonists) or, conversely, of deactivating (antagonists) specifically RARs. For example, all-trans-retinoic acid selectively activates RARs and is thus considered to be an RAR-agonist molecule.

In mice, it has been shown that the administration only of all-trans-retinoic acid topically induces a dose-dependent response of proliferation of the epidermis, with a maximum response four days after the application ("Retinoic acid provokes a regeneration-like proliferative response in murine epidermis" Arch. Dermatol. Res. 1992, 284:418–423). In accordance with this result, the response to a topical application of all-trans-retinoic acid on mouse ear is reflected, in particular, by an increase in thickness of the mouse ear. This increase in mouse ear thickness seems to be due to an increase in the thickness of the epidermis and to the appearance of a dermal oedema. This response can thus readily be measured using a machine, such as the oditest, the response being at its maximum on the fifth and sixth days after the application. This response is confirmed with all RAR-agonist molecules.

As regards RAR-antagonists, these prove to be especially advantageous in the treatment of dermatological, rheumatic, respiratory, cardiovascular, bone or ophthalmological disorders or complaints associated in particular with over-regulation (overexpression or overactivity) of RAR receptors and/or with hypervitaminosis A (presence in the body of an abnormal amount of vitamin A or metabolites thereof). Thus the advantage of finding new RAR-antagonist compounds which can inhibit the biological effects of over-regulation of RAR receptors and/or of hypervitaminosis A can be appreciated.

The Applicant has just discovered that the response of the skin of a mammal to the topical application of an RAR-agonist molecule may be inhibited by the systemic or topical application of an RAR-antagonist molecule.

Thus, the object of the present invention is to propose a simple process for identifying RAR-antagonist molecules.

This and other objects are achieved by the present invention which relates to a process for identifying RAR-antagonist molecules, characterized in that it comprises the following steps: (i) a sufficient amount of at least one RAR-agonist molecule is applied topically to a part of the skin of a mammal, (ii) a molecule capable of having an RAR-antagonist activity is administered systemically or topically to this same mammal, or to this same part of the skin of the mammal, before, during or after step (i), and (iii) the response on that part of the skin of the mammal thus treated is evaluated and compared with the response obtained on this same part of skin treated by step (i) only.

Thus, when the molecule administered is an RAR antagonist, the increase in the thickness of the part of the skin of the mammal thus treated with an RAR-agonist molecule is not observed or is reduced. An inhibition of the response is thus observed.

In practice, the mammal is a rodent such as a mouse, a rat, a guinea pig, a hamster or a rabbit.

The part of the mammal skin used can be any part of the mammal's body.

The response on that part of the skin of the mammal thus treated and to be evaluated corresponds to a clinical modification of the skin. In general, this response to be evaluated corresponds to a modification in the thickness of the part of the skin thus treated.

Thus, the thickness of the part of the skin thus treated may be measured by any method known per se.

When the part of the skin used is smooth, its thickness may be measured by folding it.

In a more practical manner, the skin of the ear is used. The thickness of the ear may then be measured by an oditest.

Obviously, the evaluation of step (iii) corresponds to a measurement of the response of the part of the skin thus treated and to a comparison of this measurement with that of the response of this same part of the treated skin, under the same conditions, with the RAR-agonist molecule alone.

The RAR-agonist molecules are preferably chosen from compounds capable of inducing the differentiation of mouse embryonic teratocarcinoma (F9) cells. Secretion of the plasminogen activator which accompanies this differentiation is an indication of the biological response of the F9 cells to these compounds. It is also known that the capacity of these compounds to induce the plasminogen activator is directly correlated with their affinity and activity on the RAR receptors endogenous to the F9 cells (Skin Pharmacol., 1990, 3, pp. 256–267).

Among the RAR-agonist molecules which induce the differentiation of F9 cells and which may be mentioned more particularly are:

all-trans-retinoic acid, 2-(5,6,7,8-tetrahydro-5,5,8,8,-tetramethyl-2-naphthyl)-6-benzo[b]thiophenecarboxylic acid, 4-[(5,6,7,8-tetrahydro-5,5,8,8,-tetramethyl-2-naphthyl)carboxamido]benzoic acid, 4-[(5,6,7,8-tetrahydro-5,5,8,8-tetramethyl-2-naphthyl)carbamoyl]benzoic acid.

In the following and in the foregoing text, the expression "via the topical route" is understood to refer to any technique for administering a product by direct application of this product to a surface (or external) part of the body, and the term "systemically" is understood to refer to any technique for administering a product via a route other than a topical route, for example enterally and/or parenterally. In the case of the systemic route, the oral route is preferably used.

The sufficient amount to be applied of an RAR-agonist molecule corresponds to that at which a response of the treated part of the skin of the mammal after step (i) is observed. Thus, preferably and depending on the nature of the RAR-agonist molecule used, this amount is in the range between 0.0001% and 2% by weight per unit volume of solution applied.

Several examples will now be given, without any limitation whatsoever being implied.

EXAMPLE 1

The test used is thus that of mouse-ear oedema induced by topical application of 2-(5,6,7,8-tetrahydro-5,5,8,8-tetramethyl-2-naphthyl) -6-benzo[b]thiophenecarboxylic acid (all-trans-retinoic acid analogue) at a concentration of 0.01% on a weight per unit volume basis. According to this model, a topical application of 2-(5,6,7,8-tetrahydro-5,5,8,8-tetramethyl-2-naphthyl)-6-benzo[b]thiophenecarboxylic acid to the ear gives rise to an inflammation which is characterized by an increase in the thickness of the mouse ear, this increase becoming maximal at the end of 5 days after the application. This response may thus be quantified by measuring the thickness of the ear by an oditest.

The exact procedure is as follows: 10 mice are first treated with 2-(5,6,7,8-tetrahydro-5,5,8,8-tetramethyl-2-naphthyl)-6-benzo[b]thiophenecarboxylic acid (compound A), carrying out a topical application to one of their ears at time t=0 with 20 ml of an acetone solution comprising 0.01% on a weight per unit volume basis of 2-(5,6,7,8-tetrahydro-5,5,8,8-tetramethyl-2-naphthyl)-6-benzo[b]thiophenecarboxylic acid. Simultaneously, 0.1%, on a weight for volume basis, of trans-7-[3-(1-adamantyl)-4-methoxyphenyl]-3,7-dimethyl-2,4,6-heptatrienoic acid (compound X) in acetone is applied topically once, to 5 (=group 2) out of the 10 mice treated with compound A, at t=0. The 5 mice which have not been treated with compound X constitute group 1. The response is quantified by measuring the thickness of the ear at t=5 or 6 days. The results are then expressed as a % of the inhibition, calculated in the following way:

$$\frac{\text{mouse-ear thickness (Group 1)} - \text{mouse-ear thickness (Group 2)}}{\text{mouse-ear thickness (Group 1)}} \times 100$$

By another test, compound X proves to be an RAR antagonist. Indeed, the antagonist activity of compound X is evaluated in the test of differentiation of mouse embryonic teratocarcinoma F9 cells (Cancer Research 43, p. 5268, 1983). This compound, tested at $10^{-6}$M, is inactive as an agonist in this test and partially or totally inhibits the effect produced by an agonist retinoid on the morphology and secretion of the plasminogen activator (the secretion of the plasminogen activator which accompanies the differentiation of the F9 cells being an indication of the biological response of the F9 cells to retinoids).

The results obtained are collated in Table 1 below.

TABLE 1

| Topical route | Dose (% w/v) | Topical route | Dose (% w/v) | Inhibition (%) |
|---|---|---|---|---|
| Compound A | 0.01 | Compound X | 0.1 | 58.60 | w/v means weight per unit volume.

Thus, it is clearly demonstrated, by means of this test, that the combination of an RAR-receptor agonist with an RAR-receptor antagonist considerably inhibits the response of the mouse ear when compared with the response induced by topical application only of an RAR-receptor ligand.

EXAMPLE 2

Exactly the same test as in Example 1 is performed, except that compound A is replaced with all-trans-retinoic acid (compound B).

The results obtained are collated in Table 2 below.

TABLE 2

| Topical route | Dose (% w/v) | Topical route | Dose (% w/v) | Inhibition (%) |
|---|---|---|---|---|
| Compound B | 0.1 | Compound X | 0.1 | 32 | w/v means weight per unit volume.

EXAMPLE 3

Exactly the same test as in Example 1 is performed, except that compound X is replaced by a compound Y: 4-[3-(1-adamantyl)-4-methoxyethoxymethoxy-phenylethynyl]benzoic acid or by a compound Z: 4-[7-(1-adamantyl)-6-methoxyethoxymethoxy-2-naphthyl]benzoic acid.

Compounds Y and Z moreover prove to be RAR antagonists, the antagonist activity of compounds Y and Z having been evaluated in the test of the differentiation of mouse embryonic teratocarcinoma F9 cells, as described in Example 1.

The results obtained are collated in Table 3 below.

TABLE 3

| Topical route | Dose (% w/v) | Topical route | Dose (% w/v) | Inhibition (%) |
|---|---|---|---|---|
| Compound A | 0.01 | Compound Y | 0.1 | 81 |
| Compound A | 0.01 | Compound Z | 0.1 | 92 | w/v means weight per unit volume.

EXAMPLE 4

Exactly the same test as in Example 1 is performed, except that compound A is replaced by compound B (as described in Example 2) and compound X is replaced by compounds Y or Z (as described in Example 3).

The results obtained are collated in Table 4 below:

TABLE 4

| Topical route | Dose (% w/v) | Topical route | Dose (% w/v) | Inhibition (%) |
|---|---|---|---|---|
| Compound B | 0.1 | Compound Y | 0.1 | 32 |
| Compound B | 0.1 | Compound Z | 0.1 | 86 |

EXAMPLE 5

Exactly the same test as in Example 1 is performed, except that compounds Z and W, replacing compound X, are administered orally in cremophor-type oil (EL 25%), instead of being applied topically, at the doses indicated in Table 5 below.

Compound W is: p-{(E)-2-[3',4'-dihydro-4',4'-dimethyl-7'-(heptyloxy)-2'H-1-benzothiopyran-6'-yl]-propenyl}benzoic acid.

Compound W moreover proves to be an RAR antagonist, the antagonist activity of this compound having been evaluated in the test of differentiation of mouse embryonic teratocarcinoma F9 cells, as described in Example 1.

The results obtained are collated in Table 5 below:

TABLE 5

| Topical route | Dose (% w/v) | Topical route | Dose (% w/v) | Inhibition (%) |
|---|---|---|---|---|
| Compound A | 0.01 | Compound Z | 30 | 45 |
| Compound A | 0.01 | Compound W | 30 | 79 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Process for identifying RAR-antagonist molecules, which comprises the following steps:
    (i) topically applying an RAR-agonist molecule to a portion of the skin of a mammal in an amount sufficient to elicit an RAR agonist response;
    (ii) systemically or topically administering a molecule putatively possessing RAR-antagonist activity to the same mammal, or to this same portion of the skin of the mammal, before, during or after step (i); and
    (iii) evaluating the skin response at said portion of the skin of the mammal after steps (i) and (ii) and comparing said response to the response obtained at the skin portion when such skin portion is not administered with said putative RAR-antagonist molecule.

2. Process according to claim 1, wherein the mammal is a rodent.

3. Process according to claim 1, wherein the portion of the mammal skin is the skin of the ear.

4. Process according to claim 1, wherein the response evaluated in step (iii) corresponds to a modification in the thickness of that part of the skin of the mammal.

5. Process according to claim 1, wherein the RAR-agonist molecule is selected from compounds capable of inducing the differentiation of mouse embryonic teratocarcinoma (F9) cells.

6. Process according to claim 5, wherein the RAR-agonist molecule used is selected from the group consisting of:
    all-trans-retinoic acid,
    2-(5,6,7,8-tetrahydro-5,5,8,8,-tetramethyl-2-naphthyl)-6-benzo[b]thiophenecarboxylic acid,
    4-[(5,6,7,8-tetrahydro-5,5,8,8,-tetramethyl-2-naphthyl) carboxamido]benzoic acid, and
    4-[(5,6,7,8-tetrahydro-5,5,8,8-tetramethyl-2-naphthyl) carbamoyl]benzoic acid.

7. Process according to claim 1, wherein systemically administering in step (ii) comprises oral administration.

8. The method of claim 2, wherein said rodent is selected from the group consisting of a mouse, rate guinea pig, hamster and rabbit.

* * * * *

UNITED STATES PATENT AND TRADEMARK OFFICE
CERTIFICATE OF CORRECTION

PATENT NO. : 5,827,500
DATED : October 27, 1998
INVENTOR(S) : Michel Demarchez et al.

It is certified that error appears in the above-identified patent and that said Letters Patent is hereby corrected as shown below:

Column 3, line 31, please change "20ml" to --20µl--.

Column 4, Table 4, please insert --w/v means weight per unit volume-- after the Table.

Column 6, line 29, please change "rate" to --rat--.

Signed and Sealed this

Eleventh Day of May, 1999

Attest:

Attesting Officer

Q. TODD DICKINSON

Acting Commissioner of Patents and Trademarks